United States Patent [19]

Otsuki et al.

[11] 4,216,323
[45] Aug. 5, 1980

[54] SEPARATION AND RECOVERY OF 1,4-DIAZABICYCLO-(2,2,2)-OCTANE

[75] Inventors: Susumi Otsuki; Shizuo Yamada, both of Shin-nanyo; Yaichro Ono, Kudamatsu, all of Japan

[73] Assignee: Toyo Soda Manufacturing Company, Limited, Yamaguchi, Japan

[21] Appl. No.: 958,398

[22] Filed: Nov. 7, 1978

[30] Foreign Application Priority Data

Nov. 22, 1977 [JP] Japan ..................................... 139414

[51] Int. Cl.² ........................................... C07D 487/18
[52] U.S. Cl. .................................................... 544/352
[58] Field of Search .......................................... 544/353

[56] References Cited

U.S. PATENT DOCUMENTS

| 3,045,018 | 7/1962 | Mascioto | 544/352 |
| 3,120,525 | 2/1964 | Muhlbauer et al. | 544/352 |
| 3,120,526 | 2/1964 | Brader, Jr. | 544/352 |
| 3,123,607 | 3/1964 | Farkas et al. | 544/352 |
| 3,152,129 | 10/1964 | Sonbert | 544/352 |
| 3,772,293 | 11/1973 | Oakes et al. | 544/352 |

*Primary Examiner*—Jose Tovar
*Attorney, Agent, or Firm*—Oblon, Fisher, Spivak, McClelland & Maier

[57] ABSTRACT

1,4-Diazabicyclo-(2,2,2)-octane is separated and recovered by adding water to a crude 1,4-diazabicyclo-(2,2,2)-octane including an alkyl pyrazine and other amines and then, separating 1,4-diazabicyclo-(2,2,2)-octane by a distillation of water and the alkyl pyrazine and a crystallization.

6 Claims, No Drawings

SEPARATION AND RECOVERY OF 1,4-DIAZABICYCLO-(2,2,2)-OCTANE

BACKGROUND OF THE INVENTION

It has been proposed a process for producing 1,4-diazabicyclo-(2,2,2)-octane by reacting an alkylene polyamine as a starting material on a catalyst such as a metal phosphate, a silica-alumina type compound in gaseous phase at 250° to 550° C.

In these processes, various amines including piperazine and alkyl piperazines as by-products are produced together with the object compound of 1,4-diazabicyclo-(2,2,2)-octane.

Accordingly, 1,4-diazabicyclo-(2,2,2)-octane is obtained by repeating separations such as distillation, cooling and drying from the resulting amines mixture.

However, alkyl pyrazines such as 2-ethyl-3-methyl pyrazine, 2-ethyl-6-methyl pyrazine and 1-propyl pyrazine among the amines mixture, have boiling points similar to the boiling point of 1,4-diazabicyclo-(2,2,2)-octane whereby it is difficult to obtain a pure 1,4-diazabicyclo-(2,2,2)-octane by a simple distillation.

These alkyl pyrazines remain in a process solution including 1,4-diazabicyclo-(2,2,2)-octane to accumulate the alkyl pyrazines in the process solution. Sometimes, it is necessary to stop the operation whereby the process for producing 1,4-diazabicyclo-(2,2,2)-octane is interrupted.

In the process for producing 1,4-diazabicyclo-(2,2,2)-octane, a separation of the alkyl pyrazines from the process solution is important and indispensable to obtain 1,4-diazabicyclo-(2,2,2)-octane having high purity and to overcome a trouble in the process. Moreover, it is desired to develop a separation of the alkyl pyrazines so as to decrease a loss of 1,4-diazabicyclo-(2,2,2)-octane.

SUMMARY OF THE INVENTION

It is an object of the present invention to overcome the disadvantages and to provide a separation and recovery of 1,4-diazabicyclo-(2,2,2)-octane from a crude 1,4-diazabicyclo-(2,2,2)-octane including an alkyl pyrazine.

The foregoing and other objects of the present invention have been attained by adding water to a crude 1,4-diazabicyclo-(2,2,2)-octane including an alkyl pyrazine such as a process solution of 1,4-diazabicyclo-(2,2,2)-octane obtained in a step of producing 1,4-diazabicyclo-(2,2,2)-octane, and then, separating 1,4-diazabicyclo-(2,2,2)-octane by a distillation of water and the alkyl pyrazine and a crystallization and a washing with an inert solvent.

DETAILED DESCRIPTION OF THE PREFERRED EMBODIMENTS

The reaction mixture and the process solution including 1,4-diazabicyclo-(2,2,2)-octane will be illustrated.

In the reaction mixture used in the present invention, various amines such as triethylene diamines, piperadines, alkyl pyrazines are included. The alkyl pyrazines having boiling point similar to the boiling point of 1,4-diazabicyclo-(2,2,2)-octane remarkably affect in the recovery of 1,4-diazabicyclo-(2,2,2)-octane from the reaction mixture.

When water is added to the reaction mixture, the alkyl pyrazines having similar boiling point are separated by a distillation with water from the solution including 1,4-diazabicyclo-(2,2,2)-octane and a fraction of a crude 1,4-diazabicyclo-(2,2,2)-octane having relatively high purity can be obtained by a following distillation. Thus, a separation efficiency in the step of the cooling recovery of 1,4-diazabicyclo-(2,2,2)-octane is significantly improved.

The method of the present invention can be also improved in a recovery of 1,4-diazabicyclo-(2,2,2)-octane from a filtrate obtained in a separation and a recovery of 1,4-diazabicyclo-(2,2,2)-octane by cooling the fraction of the crude 1,4-diazabicyclo-(2,2,2)-octane.

The filtrate includes 1,4-diazabicyclo-(2,2,2)-octane and the other amines such as alkyl pyrazines.

When the other amines are distilled off so as to concentrate 1,4-diazabicyclo-(2,2,2)-octane, if water is added before the distillation, the alkyl pyrazines which can not be separated from 1,4-diazabicyclo-(2,2,2)-octane by a conventional distillation, can be distilled off together with the other amines to obtain a crude 1,4-diazabicyclo-(2,2,2)-octane having only small alkyl pyrazine content.

When the crude 1,4-diazabicyclo-(2,2,2)-octane is cooled, the amount of crystalline 1,4-diazabicyclo-(2,2,2)-octane is increased in comparison with the case including much alkyl pyrazines. The resulting crystals include 1,4-diazabicyclo-(2,2,2)-octane and other amines and the crystals are separated from a filtrate and are washed with an inert solvent such as alcohols e.g. methanol to obtain 1,4-diazabicyclo-(2,2,2)-octane having high purity.

The filtrate also includes 1,4-diazabicyclo-(2,2,2)-octane whose content is reduced since the alkyl pyrazines are substantially removed by the distillation.

Alkyl pyrazines are in a liquid form at room temperature and dissolve 1,4-diazabicyclo-(2,2,2)-octane at relatively high ratio. When alkyl pyrazines are previously removed from the mixture of amines including 1,4-diazabicyclo-(2,2,2)-octane, the recovery efficiency is increased in the recovery of 1,4-diazabicyclo-(2,2,2)-octane by cooling it.

In this step, the amount of water added before the distillation can be as maximum, about 300 wt.% to total distillation components and about 50 times to the amount of alkyl pyrazines and it is preferably in a range of 1 to 300 wt.% especially 10 to 150 wt.% to total distillation components and in a range of 0.5 to 50 times to the amount of alkyl pyrazines.

The present invention will be further illustrated by certain examples which shall be interpreted as illustrative and not in a limiting sense.

EXAMPLE 1

Water was added at a ratio of 60 wt.% to a reaction mixture of 30 g (30 wt.%) of 1,4-diazabicyclo-(2,2,2)-octane, 6 g (6 wt.%) of alkyl pyrazines and 64 g (64 wt.%) of the other amines which was obtained by a reaction for producing 1,4-diazabicyclo-(2,2,2)-octane under contacting an alkylene polyamine with a catalyst in gaseous phase. The mixture was heated in a distillation tower to distill off an oil phase having main components of 3.6 g of alkyl pyrazines and a water phase including a small amount of amines from a top of the distillation tower. The composition of a bottom residue included 30 g (39 wt.%) of 1,4-diazabicyclo-(2,2,2)-octane, 2.4 g (3 wt.%) of alkyl pyrazines and 44.8 g (58 wt.%) of the other amines.

The bottom residue was cooled to room temperature to obtain 28 g of crude crystals having 22.5 g of 1,4-diazabicyclo-(2,2,2)-octane and 42 g of a filtrate having 7.5 g of 1,4-diazabicyclo-(2,2,2)-octane and 2.4 g of alkyl pyrazines. The crude crystals were washed with methanol to obtain 1,4-diazabicyclo-(2,2,2)-octane having high purity at recovery coefficient of 75%.

EXAMPLE 2

Water was added at a ratio of 25 wt.% to a process solution of 53 g (53 wt.%) of 1,4-diazabicyclo-(2,2,2)-octane, 20 g (20 wt.%) of alkyl pyrazines and 27 g (26 wt.%) of the other amines having lower boiling points which was obtained in the process for producing 1,4-diazabicyclo-(2,2,2)-octane. The mixture was heated in a distillation tower to distill off an oil phase having main components of alkyl pyrazines and a water phase including a small amount of amines from a top of the distillation tower. The bottom residue was cooled to 20° to 25° C. to obtain 52.5 g of crude crystals having 42 g (80 wt.%) of 1,4-diazabicyclo-(2,2,2)-octane and 27.5 g of a filtrate having 11 g (40 wt.%) of 1,4-dizabicyclo-(2,2,2)-octane. The crude crystals were washed with methanol to obtain 1,4-dizabicyclo-(2,2,2)-octane having high purity at a recovery coefficient of 80 wt.%.

REFERENCE 1 A process solution having 53 g (53 wt.%) of 1,4-diazabicyclo-(2,2,2)-octane and 20 g (20 wt.%) of alkyl pyrazines was heated in a distillation tower to distill off amines having lower boiling points and a solvent and to obtain a bottom residue as a concentrated mixture.

The concentrated mixture was cooled to 20°to 25° C. to obtain 55.7 g of crude crystals having 33.4 g (60 wt.%) of 1,4-diazabicyclo-(2,2,2)-octane and 31.6 g of a filtrate having 19.6 g (62 wt.%) of 1,4-diazabicyclo-(2,2,2)-octane.

The recovery coefficient of 1,4-diazebicyclo-(2,2,2)-octane was 63%.

EXAMPLES 3 to 9

Water was added before each distillation of the amines mixtures having the compositions shown in Table and 1,4-diazabycyclo-(2,2,2)-octane was recovered. The results are shown in Table. As the references, the distillations of the same compositions were carried out without adding water.

The results are also shown in Table.

Table

| Exp. | Compostion of feed (%) | | | Ratio of water to feed (%) | Recovery coefficient of 1,4-diazacicyclo-(2,2,2)-octane (%) |
| --- | --- | --- | --- | --- | --- |
|  | DABO | AP | Other |  |  |
| Exp. 3 | 49.2 | 15.5 | 35.3 | 100 | 76.2 |
| Ref. 3' | 49.2 | 15.5 | 35.3 | 0 | 68.4 |
| Exp. 4 | 37.9 | 14 | 48.1 | 100 | 83.3 |
| Ref. 4' | 37.9 | 14 | 48.1 | 0 | 62.9 |
| Exp. 5 | 42.0 | 14.4 | 43.6 | 10 | 73.5 |
| Ref. 5' | 42.0 | 14.4 | 43.6 | 0 | 65.7 |
| Exp. 6 | 42.0 | 14.4 | 43.6 | 107 | 79.3 |
| Ref. 6' | 42.0 | 14.4 | 43.6 | 0 | 65.7 |
| Exp. 7 | 31.8 | 10.8 | 57.4 | 70 | 81.5 |
| Ref. 7' | 31.8 | 10.8 | 57.4 | 0 | 65.7 |
| Exp. 8 | 76.2 | 10 | 13.8 | 20 | 96.3 |
| Ref. 8' | 76.2 | 10 | 13.8 | 0 | 86.8 |
| Exp. 9 | 39.2 | 20.5 | 40.3 | 100 | 70.6 |
| Ref. 9' | 39.2 | 20.5 | 40.3 | 0 | 47.5 |

DABO: 1,4-diazabicyclo-(2,2,2)-octane
AP: alkyl pyrazines

What is claimed is:

1. A method of separating and recovering 1,4-diazabicyclo-(2,2,2)-octane which comprises adding water to a crude 1,4-diazabicyclo-(2,2,2)-octane including an alkyl pyrazine and then, separating 1,4-diazabicyclo-(2,2,2)-octane by a distillation of water and the alkyl pyrazine and a crystallization.

2. A method according to claim 1 wherein said crude 1,4-diazabicyclo-(2,2,2)-octane is a reaction mixture obtained by reacting an alkylene polyamine in the presence of a catalyst in gaseous phase.

3. A method according to claim 1 wherein said crude 1,4-diazabicyclo-(2,2,2)-octane is a process solution.

4. A method according to claim 1 wherein said crude 1,4-diazabicyclo-(2,2,2)-octane is a bottom residue obtained by distilling off amines having lower boiling points in a distillation tower.

5. A method according to claim 1 wherein water is added at a ratio of 1 to 300 wt.% total amines of said crude 1,4-diazebicyclo-(2,2,2)-octane.

6. A method according to claim 1 wherein water is added at a ratio of 0.5 to 50 times to an amount of alkyl pyrazines.

* * * * *